(12) United States Patent
Behzadi

(10) Patent No.: US 10,299,930 B2
(45) Date of Patent: May 28, 2019

(54) MECHANICAL ASSEMBLY INCLUDING EXTERIOR SURFACE PREPARATION

(71) Applicant: Kambiz Behzadi, Pleasanton, CA (US)

(72) Inventor: Kambiz Behzadi, Pleasanton, CA (US)

(*) Notice: Subject to any disclaimer, the term of this patent is extended or adjusted under 35 U.S.C. 154(b) by 0 days.

(21) Appl. No.: 15/458,586

(22) Filed: Mar. 14, 2017

(65) Prior Publication Data

US 2017/0354505 A1    Dec. 14, 2017

Related U.S. Application Data

(60) Provisional application No. 62/348,987, filed on Jun. 12, 2016.

(51) Int. Cl.
*A61F 2/36* (2006.01)
*A61F 2/30* (2006.01)

(52) U.S. Cl.
CPC .......... *A61F 2/3609* (2013.01); *A61F 2/3662* (2013.01); *A61F 2002/30014* (2013.01); *A61F 2002/3082* (2013.01); *A61F 2002/30146* (2013.01); *A61F 2002/30332* (2013.01); *A61F 2002/30347* (2013.01); *A61F 2002/30367* (2013.01); *A61F 2002/30985* (2013.01); *A61F 2002/365* (2013.01)

(58) Field of Classification Search
CPC ...... A61F 2/28; A61F 2/30; A61F 2/38; A61F 2/3609; A61F 2/3662
See application file for complete search history.

(56) References Cited

U.S. PATENT DOCUMENTS

| | | |
|---|---|---|
| 2008/0091271 A1 | 4/2008 | Bonitati et al. |
| 2008/0234833 A1 | 9/2008 | Bandoh et al. |
| 2013/0211535 A1 | 8/2013 | Cueille |
| 2014/0363481 A1* | 12/2014 | Pasini ............... A61C 13/0004 424/423 |
| 2015/0216668 A1 | 8/2015 | Smith |
| 2017/0354505 A1 | 12/2017 | Behzadi |

OTHER PUBLICATIONS

International Search Report regarding International application No. PCT/US2017/037042 dated Oct. 6, 2017.
Written Opinion of the International Searching Authority regarding International application No. PCT/US2017/037042 dated Oct. 6, 2017.

* cited by examiner

*Primary Examiner* — Jason-Dennis N Stewart
(74) *Attorney, Agent, or Firm* — Patent Law Offices of Michael E. Woods; Michael E. Woods

(57) ABSTRACT

A system and method for improving mechanical assemblies, such as prosthetic implants, intended to be installed in living tissue such as bone. Force-imparting devices are adapted and may include angularity, which may be introduced with specialized additive manufacturing, which may impart congruent cross-sections while providing variable stiffness. In some cases, the variable stiffness may be "stretchy" in a longitudinal direction and "rigid" in a radial directional which may provide an assembly bias. Additive manufacturing may allow the material of a prosthesis to be varied (e.g., density/porosity) to create variable stiffness over a length.

10 Claims, 12 Drawing Sheets

MECHANICAL ASSEMBLY INCLUDING EXTERIOR SURFACE PREPARATION

CROSS REFERENCE TO RELATED APPLICATIONS

This application claims benefit of U.S. Patent Application No. 62/348,987 filed 12 Jun. 2016, the contents of which are hereby expressly incorporated in its entirety for all purposes.

FIELD OF THE INVENTION

The present invention relates generally to mechanical assemblies installed into living tissue, and more specifically, but not exclusively, to improvements in prosthetic assemblies installed into bone tissue.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Historically, early hip replacement consisted of a non-modular femoral head with a single neck option, the so-called "monobloc". This meant that restoring the leg length and offset was difficult, and may have resulted in instability and abductor dysfunction. As a result, modularity was introduced into the design of hip prosthesis and has become increasingly common in the last two decades. Modularity can be exhibited at the junction between the head and the neck, and at the junction between the trunnion (neck) and the body. The neck head junction typically consists of a trunnion, which has a machined taper allowing for an interference fit. The taper interface is where the femoral head (female taper surface) attaches to the trunnion (male taper) of the femoral stem. This optionality is extremely attractive to the surgeon allowing the ability to more accurately restore leg length, offset, and produce good stability independent of femoral stem fixation. Taper corrosion however, has recently become a clinical issue.

Trunnionosis is defined as wear of the femoral head-neck interface and has been acknowledged as a source of total hip arthroplasty (THA) failure. This phenomena appears to have gained prevalence with newer THA implant designs, particularly when modularity was introduced.

Modularity allows for better intraoperative restoration of leg length and control of hip offset, but while this enables a more customized fit for the patient, it may have untoward effects. This modularity at times may play a role in increased wear and mechanical insufficiency at the trunnion, ultimately leading to revision. By some estimates, trunnionosis accounts for up to 3% of all revision procedures. The exact cause of trunnionosis, which is likely multifactorial, currently remains poorly understood. It is postulated that contributing factors include wear between metal on metal modular junctions, corrosion and fretting damage, and release of metal ions from affected components. Additionally different implant designs and geometries have demonstrated a predisposition to trunnion failure. Although the exact cause of the recent increase of corrosion related complications is unknown, some have hypothesized that having differing alloys at the modular junction, which are under high loads, may lead to increased corrosion and fretting, i.e.: use of cobalt chrome femoral head (CoCr) on Titanium trunnion.

What is needed is a system and method for improving mechanical assemblies, such as prosthetic implants, intended to be installed in living tissue such as bone.

BRIEF SUMMARY OF THE INVENTION

Disclosed is a system and method for improving mechanical assemblies, such as prosthetic implants, intended to be installed in living tissue such as bone.

The following summary of the invention is provided to facilitate an understanding of some of the technical features related to prosthesis manufacture and assembly, and is not intended to be a full description of the present invention. A full appreciation of the various aspects of the invention can be gained by taking the entire specification, claims, drawings, and abstract as a whole. The present invention is applicable to other implants and mechanical assemblies.

Some embodiments of the present invention may include a system and method for improving mechanical assemblies, such as prosthetic implants, intended to be installed in living tissue such as bone. Force-imparting devices are adapted and may include angularity, which may be introduced with specialized additive manufacturing, which may impart congruent cross-sections while providing variable stiffness. In some cases, the variable stiffness may be "stretchy" in a longitudinal direction and "rigid" in a radial directional which may provide an assembly bias. Additive manufacturing may allow the material of a prosthesis to be varied (e.g., density/porosity) to create variable stiffness over a length.

Some embodiments of the present invention may include one or more of: a) an implementation of a force imparting machine that delivers standardized force impulses (e.g., magnitude and frequency) at a precise direction (co-axial); b) an implementation of a design for a trunnion head and trunnion stem interface, with the introduction of angularity (sharp angles) and hence "early guidance system" protecting against macro and (subsequently) micro mis-alignment; c) an implementation of a trunnion through a different manufacturing technique (e.g., additive manufacturing possibly including "3D printing" or preform) rather than subtractive techniques; d) an implementation of multidimensional differential stiffness of a trunnion that more closely resembles one or more mechanical properties of the replaced tissue (e.g., a human femoral neck that may be stiffer on a load bearing medial neck and more elastic on a tensile lateral side; e) an implementation of a femoral head that can be made with two-dimensional differential stiffness (e.g., cross-helical arrangement in the eel's skin) or (longitudinal struts that are more flexible and horizontal bands that are more rigid) in order to allow undulatory motion and a preference for insertion; and f) an implementation of a controlled stiffness of implants, such as by changing a modulus of elasticity of the prosthesis material (e.g., metal) by controlling a density and a porosity of the crystalline metal vis-à-vis 3D printing.

Multi-dimensional prosthesis can address many of current problems by mimicking natural engineering of the tissue receiving the mechanical assembly prosthesis. Specifically, certain parts of our proximal femur is very stiff and certain parts are less stiff and more flexible. Simulation of these properties in the prosthetic femoral stem/neck/head junction may alleviate many of the unwanted wear patterns currently experienced in installed base.

A mechanical interface between a first prosthesis component and a second prosthesis component, the first prosthesis component including a cavity and the second prosthesis component including an extension to engage the cavity and produce a mechanical join, including: a first mating taper wall of the cavity having a first cross-sectional profile wherein the first cross-sectional profile is non-circular; and a second mating taper wall of the extension having a second-cross-sectional profile wherein the second cross-sectional profile is complementary to the first cross-sectional profile.

A method for constructing a set of mating components of a modular prosthesis, including: a) producing a first component including a cavity; b) producing a second component including an extension configured to engage the cavity; c) defining, during the first component producing step a), the cavity having a first mating taper wall including a first cross-sectional profile wherein the first cross-sectional profile is non-circular; and d) defining, during the second component producing step b), the extension having a second mating taper wall including a second cross-sectional profile wherein the second cross-sectional profile is complementary to the first cross-sectional profile.

A structure for at least a partial insertion into a portion of a bone having a bone variable stiffness profile, including: a first portion configured for installation into the portion of bone, the first portion including a first portion variable stiffness profile simulating the bone variable stiffness profile.

A method for producing a prosthesis to be installed relative to a portion of a bone having a bone variable material properties profile configuring a stiffness profile for the bone, including: a) manufacturing additively a portion of the prosthesis; and b) changing a set of material properties during said manufacturing step a) to produce a variable material properties profile of said portion of the prosthesis simulating the bone variable material properties profile.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
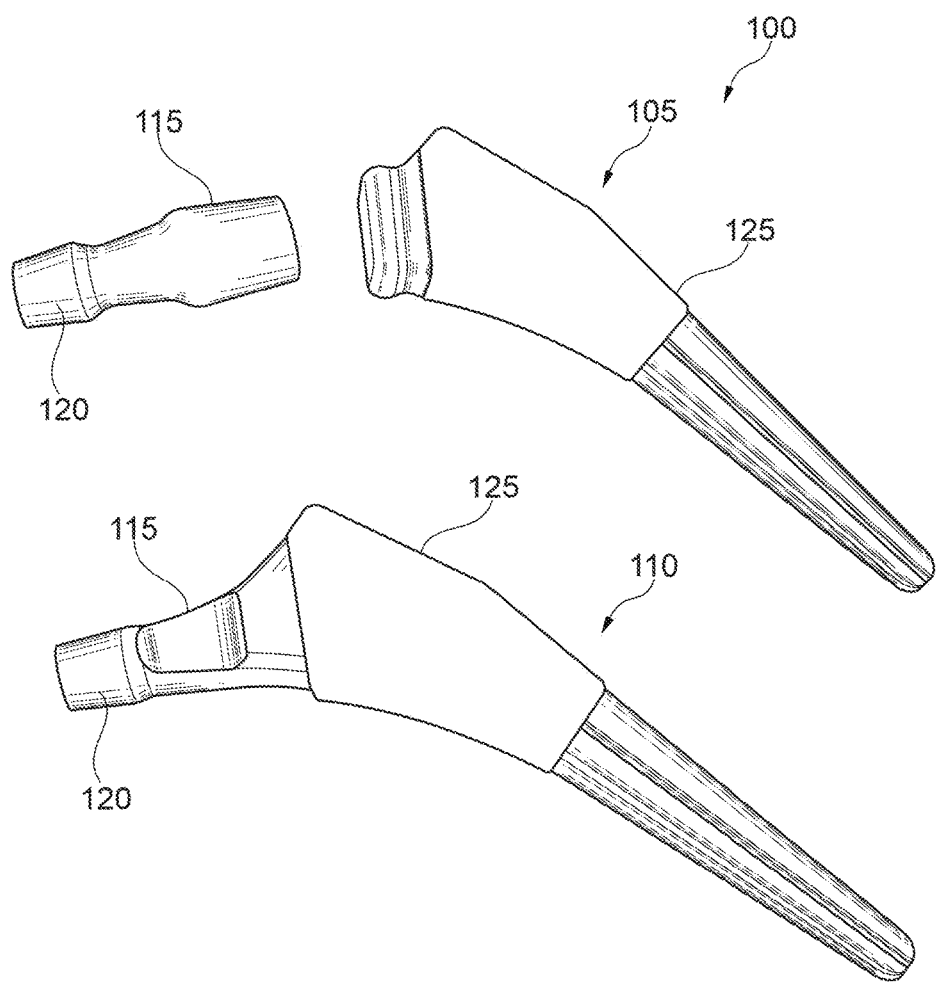
FIG. 1 illustrates a modular prosthesis assembly in both an unassembled mode and an assembled mode.

Embodiments of the present invention provide a system and method for improving mechanical assemblies, such as prosthetic implants, intended to be installed in living tissue such as bone. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "material properties" means a set of measures of a material that may include a composition, an arrangement, a molecular structure, a crystalline structure, a porosity, a grain size, and other non-geometric bulk or macroscopic properties and attributes of the material that influence and set a stiffness profile or other bulk mechanical property. Gross, or bulk, modifications to geometry may be used to provide a varying stiffness profile but it lacks an ability to simulate that of bone with which a prosthesis, or portion thereof, interacts. Variation in material properties, may be accomplished a scale barely perceptible, if at all, to a naked eye, and that aggregation of varied material properties are better able to more closely simulate the material properties of the bone with which it interacts. It being possible that any mismatches, even potentially small localized stiffness mismatches, may contribute to problems experienced by various conventional prosthesis installations including stress shielding and bone resorption.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

There is a widely held belief among some that the mechanism of taper corrosion is best characterized as mechanically assisted crevice corrosion. Fretting initialized crevice corrosion in tapers is a complex problem and the severity is likely dependent on multiple factors. Corrosion has been associated with clinical complications, such as elevated metal ion levels, persistent pain, tissue damage, and early implant failure.

Some common causes related to failure include the recent use of large femoral heads which influence torsional forces at the trunnion/taper interface, and use of shorter and more flexible trunnions (inspired to enhance motion and decrease instability). Modern prosthetic designs tend to have shorter and slimmer trunnions. This is thought to increase the impingement free range of motion by reducing the trunnion skirt. This does however mean that the base of the trunnion now sits very close to the taper, which may lead to an increase in edge loading at the trunnion base. In addition, the slimmer and smaller diameter taper means that the surface area of contact between the taper and the trunnion is less. This may reduce the chance of a successful interference fit and thus increase the potential for micro motion and fretting.

Certain solutions have been proposed to address this problem including the use of ceramic heads, which have mitigated the metal corrosion, however, use of ceramic femoral heads has not completely eliminated metal corrosion from the head-neck taper. This fact points out other mechanical factors that may be significant in this problem, including the "taper impaction technique" and "engagement of the modular taper interface".

FIG. 1 illustrates a modular prosthesis assembly 100 in both an unassembled mode 105 and an assembled mode 110. Mode 105 illustrates two components of assembly 100: a neck 115 which includes a trunnion 120 and a body 125 (sometimes may be referred to as a stem in specific assemblies 100).

Figure 2:
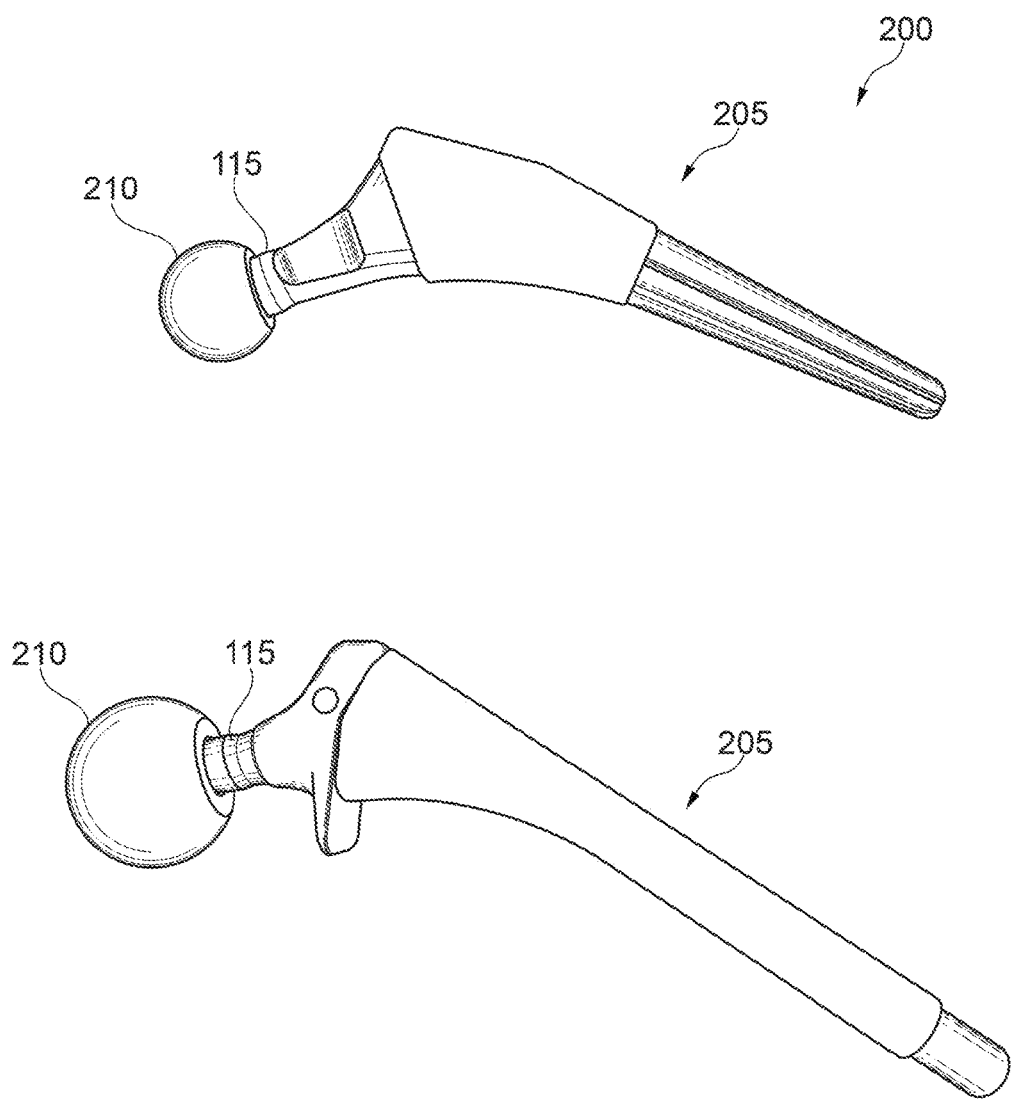
FIG. 2 illustrates a set of representative modular prosthesis assemblies in the assembled mode including a ball head portion.

FIG. 2 illustrates a set of representative modular prosthesis assemblies 200 in a completely assembled mode 205, each assembly 200 including a head 210 mechanically joined to neck 115 using trunnion 120 engaging an aperture (not shown) in head 210. The different assemblies 200 illustrate different dimensional parameters for the components of each respective assembly.

Taper locking for fixing a modular ball head onto the metal stem in total hip arthroplasty (THR) has been introduced more than 30 years ago and is now the solely used design concept of modern modular hip systems. For that purpose, the male stem taper as well as the female head taper use similar taper angels achieving close contact of the components and strong interlocking forces. Due to the fact that all manufacturing processes underlie deviations within their tolerance regime, it is nearly impossible to created ball head and stem tapers of identical taper angle, which could create a so called "line to line contact" of the components. Instead, assuming those small differences of the taper angles, the initial contact of the components will always occur at one clear end of their tapers—at the proximal end, if the stem taper is smaller than the head taper (negative mismatch), and at the distal end if the stem taper is larger than the head taper (positive mismatch).

Figure 3:
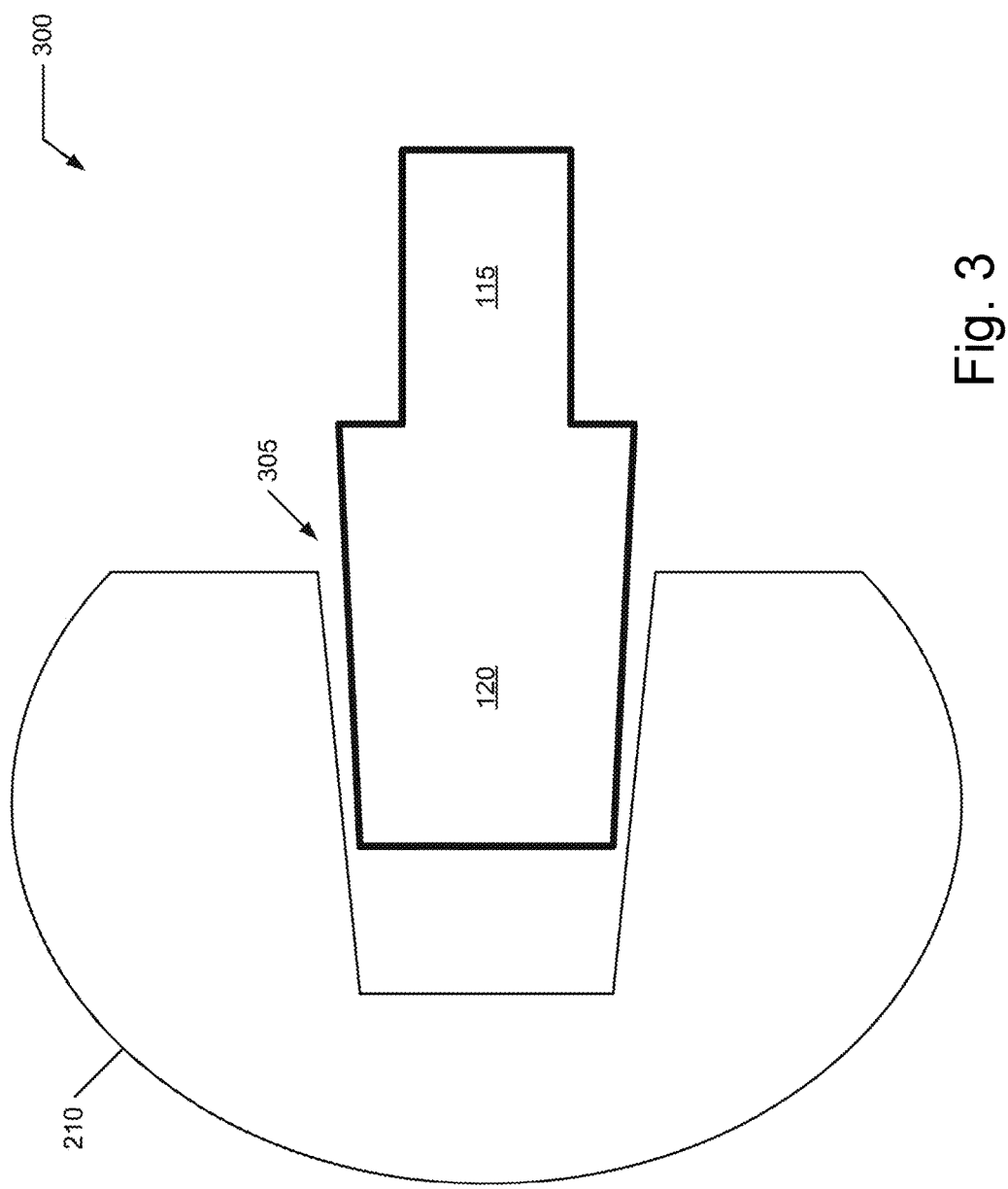
FIG. 3 illustrates a negative mismatch of a taper joinder for an assembled prosthetic assembly.

FIG. 3 illustrates a mechanical coupling portion 300 of an assembly 200 in which there is a negative mismatch of a taper joinder. Head 210 includes an aperture 305 that, ideally, would have a taper of the interior receiving surface that would be a very close match with a taper of an exterior mating surface of trunnion 120. The taper joinder is the mechanical coupling of the interior surface and the exterior surface.

Figure 4:
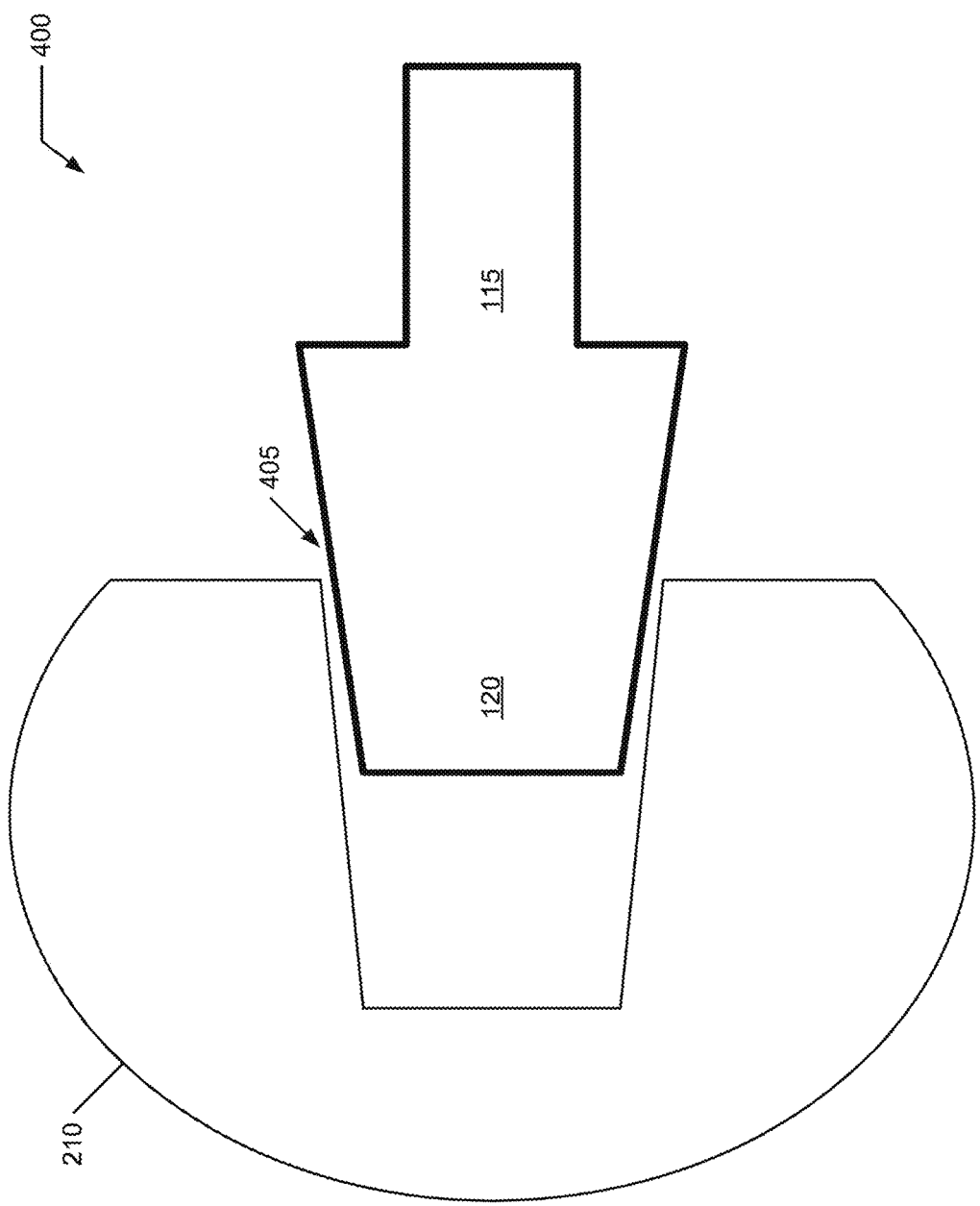
FIG. 4 illustrates a positive mismatch of a taper joined for an assembled prosthetic assembly.

FIG. 4 illustrates a mechanical coupling portion 400 of an assembly 200 in which there is a positive mismatch of a taper joinder. Head 210 includes an aperture 405 that, ideally, would have a taper of the interior receiving surface that would be a very close match with a taper of an exterior mating surface of trunnion 120. The taper joinder is the mechanical coupling of the interior surface and the exterior surface.

Figure 5:
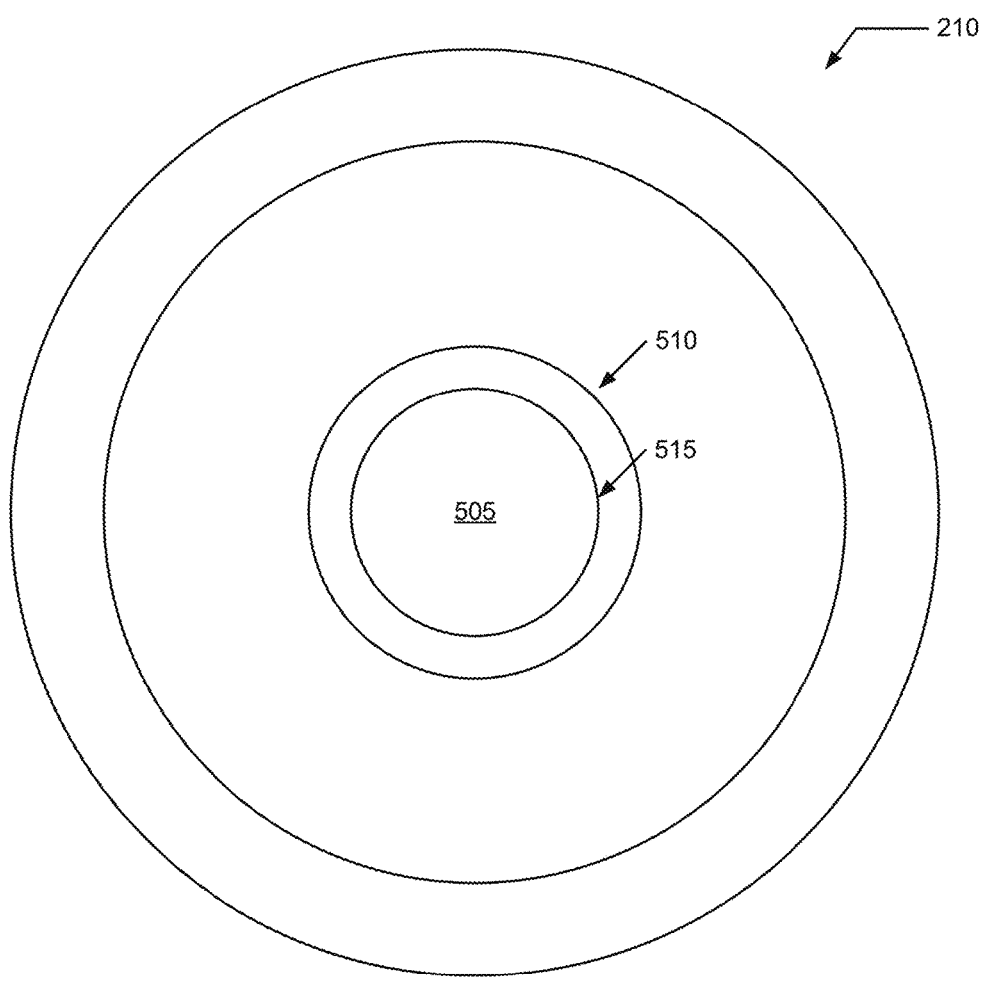
FIG. 5 illustrates a plan view of a joinder opening in a head for a prosthetic assembly.

FIG. 5 illustrates a plan view of a head 210 including an aperture 505. Aperture 505 includes an opening 510 that narrows to a termination 515, with the taper depending upon a depth of the aperture 505 and a difference between radii of opening 510 and termination 515. A mismatch depends upon a relationship of this taper to the taper of a mating trunnion 120 inserted within aperture 505.

It is also possible to define head and stem taper angel (mean and tolerance) in such a way that their difference is positive or negative over the whole tolerance field. In that case, the initial contact of the components will always occur at the same taper end, leading to an angular gap of deviating size between the components always opening up into the same direction. An inevitable property of head-taper junctions is the occurrence of micro-motion, so called fretting, within the angular gap under alternating loads which can reach nine times the body weight. These micro motions include reversible and irreversible closing and opening movements of the angular gap, increasing and decreasing the contact area, and sliding movements of the component taper surfaces along the taper axis. Mechanical stresses subsequently induced in the components at and below the surface are compression, tension, and shear stresses. Besides mechanical stresses there may also be physio-chemical interactions of the surfaces and materials considering the fluid, water-containing environment in the human body. Fretting corrosion is related to relative interface shear motion and fluid ingress, which may vary with contact force and area. Some have hypothesized that assembly forces modify the extent and distribution of the surface contact area at the taper surface interface. Increased assembly forces could generate sufficient friction resistance at the interface to prevent local fretting, and may also improve sealing of the interface and limit fluid ingress. Design factors that may modulate this interaction are material and geometry of the taper heads. Both surface design and assembly force thus seem to play a role in corrosion patterns by influencing contact pressure and relative motion.

Specific weaknesses with the current design for modularity may include two factors, which involves the use of the Morse taper. The first factor involves the method of impaction in the operating room. The taper mechanism has a positive or negative mismatch by design. The surgeon typically bangs on head 210 with a plastic tamp to implant head 210 onto trunnion 120. Force is a vector with both a magnitude and a direction. The surgeon has no way to precisely and repeatably control either the magnitude or the direction of these forces. The method of impaction of head 210 on to trunnion 120 (or neck 115 on to body 125) is very crude. It is highly likely that since the force imparted is not applied co-axially, that the torsional forces created by use of the mallet and tamp produce an asymmetrical fit of the head (bore) on the trunnion. This phenomena creates surface contact between the head and the trunnion that is asymmetrical, leading to: 1) instability, increased micro-motion, and fretting, and 2) increased contact stresses leading to loss of protective metal-oxide film referred to as passivation. These factors collectively lead to "mechanically assisted crevice corrosion" and thus are believed to be less desired. Some embodiments of the present invention may include a method of impaction of head 210 onto trunnion 120 using an improved technique. Some embodiments may include a prototype to allow quantifiable delivery of force in a coaxial fashion.

The second factor with the Morse taper as a design for modularity in hip implants (and all orthopedic implants in general) is the fact just prior to seating of the implant, for example 200 microns beforehand seating of head 210 onto trunnion 120, there is significant motion and freedom in both rotational and angular planes. This may be a problem that is more pronounced as trunnion 120 becomes shorter and it is definitely more obvious with neck/body joinders, which often includes more of an oblong shaped taper.

This "freedom of motion" just before hand insertion may allow "mal-alignment" of the implants (head 210 on to neck 115) or (neck 115 on to body 125). There is essentially no structural guidance for the two components to be "keyed" into each other. At a macroscopic level the surgeon thinks and feels there is a "perfect" fit. However, at a microscopic level there is potential for large axial and rotatory mis-alignment of the two components. This mis-alignment is maintained as head 210 is tamped into place for press-fit fixation, however, leads to poor asymmetrical surface contact area, more micro-motion and fretting and hence corrosion.

While a Morse's taper may be satisfactory in many contexts, as a joinder mechanism for an implant it may be insufficient as noted herein. In a non-implant environment, it may be easier to employ a number of adhesives, epoxies, and the like which are not used in the context for assembly of an implant.

Some embodiments of the present invention may include a new method of production and design for the trunnion in an implant, such as for a femoral implant. 3D printing is becoming useful in many fields, including orthopedics. 3D printing is utilized to produce custom guides and implants and more recently utilized to produce standard prosthesis such as the acetabular cups. Some embodiments of the present invention may include a modular prosthesis assembly, and more specifically may include a component having a femoral stem and in particular the trunnion of the component be produced with 3D printing. In that way several advantages may be attained: 1) in some cases manufacturing tolerances of the trunnion and the mating (head) bore interface can be more accurate and potentially significantly lower than +/−0.015 degrees in current manufacturing techniques; and 2) when the taper junction can be created with 3D printing, some embodiments may introduce complementary angularities into the design of the taper and bore. For example, when a trunnion is created with a cross-section as a polygon (e.g., a regular or irregular plane figure having N sides, N=3, 4, 5, 6, 7, 8, 9, 10, or more, and a cross-section of the receiving bore is complementary over its lengths, that the components will begin to align and engage at a much farther distance, (i.e.: 1000 microns as opposed to 200 microns), as the hand seating of the components are attempted.

Figure 6:
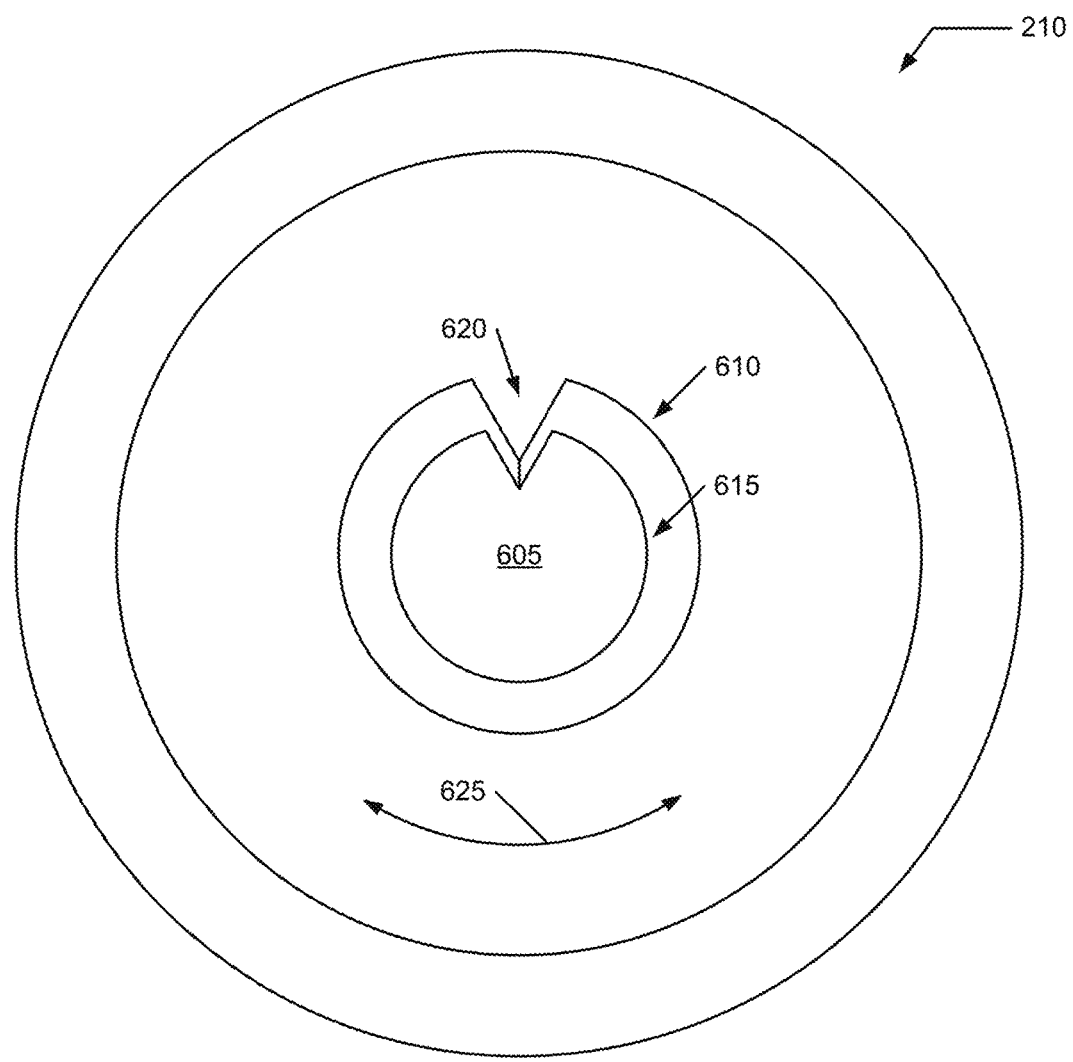
FIG. 6 illustrates a plan view of a first alternative joinder opening.

FIG. 6 illustrates a plan view of a head 210 including an aperture 605. Aperture 605 includes an opening 610 that narrows to a termination 615, with the taper depending upon a depth of the aperture 605 and a difference between "radii" of opening 610 and termination 615. Aperture 605 includes one or more guiding structures 620 that may extend some or all of a depth of aperture 605, sometimes referred to herein as a key. Structure 620 helps to limit a rotation 625 of a trunnion 120 coupled within aperture 605 and allows for help in guiding the trunnion as it is being disposed within aperture 605. When there are two or more guiding structures 620 may be disposed at periodic (e.g., 180 degrees apart for two, 120 degrees for three, 90 degrees for four, and the like) or aperiodic at irregular locations around a perimeter of aperture 605. Almost any discontinuity in a perimeter profile may serve as a key, including male, female, neutral (e.g., flat) extensions.

Figure 7:
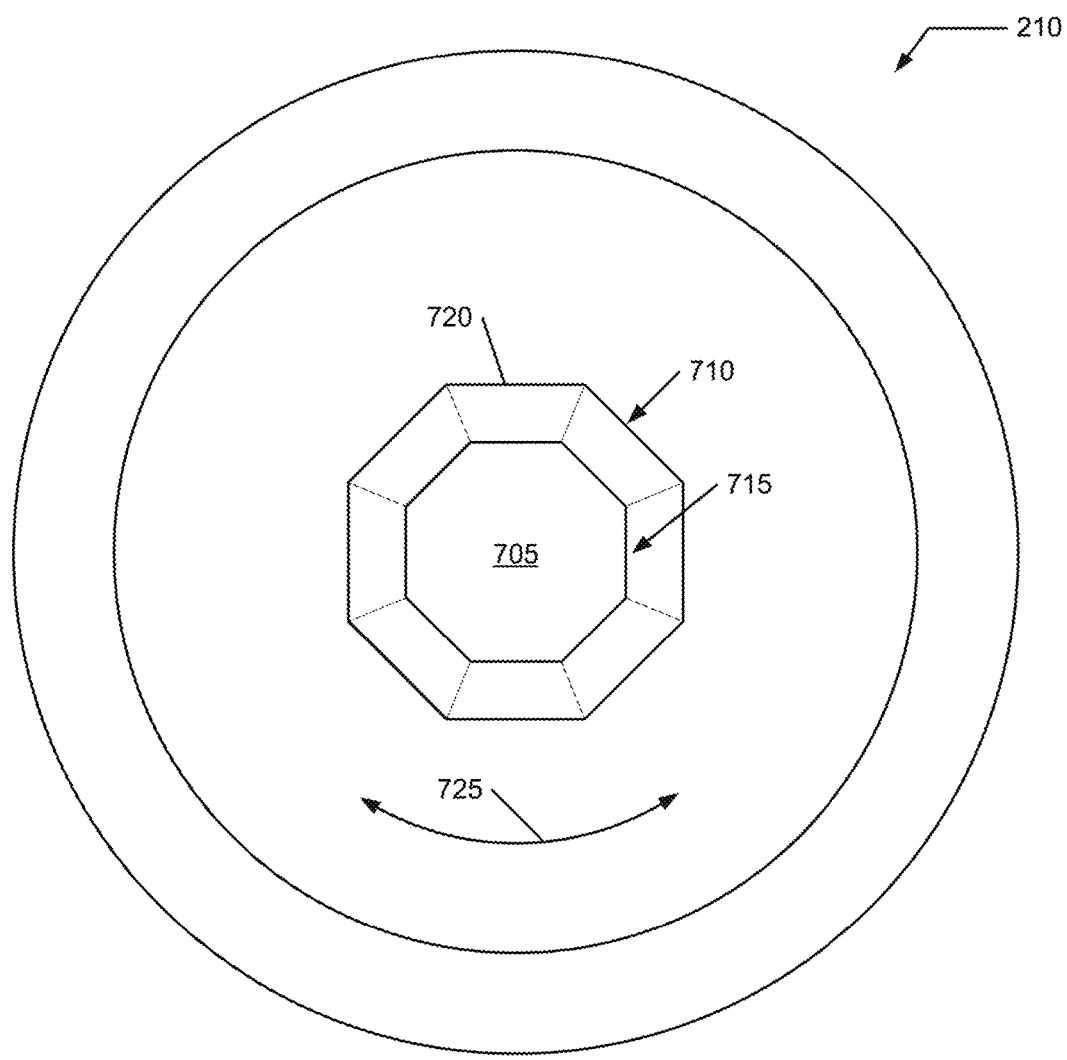
FIG. 7 illustrates a plan view of a second alternative joinder opening.

FIG. 7 illustrates a plan view of a head 210 including an aperture 705. Aperture 705 includes an opening 710 that narrows to a termination 715, with the taper depending upon a depth of the aperture 705 and a difference between "radii" of opening 710 and termination 715. Aperture 705 may be shaped as a polygon 720 (regular or irregular of N number of sides, N=3, 4, 5, 6, 7, 8, 9, 10, or more) that may extend some or all of a depth of aperture 705. Polygon 720 helps to limit a rotation 725 of a trunnion 120 coupled within aperture 705 and allows for help in guiding the trunnion as it is being disposed within aperture 705.

A sort of "guiding trail" would be inherently designed into the prosthesis, protecting against angular and rotatory misalignment. The introduction of sharp angles in the trunnion would assure proper seating and mating of the two implants without mis-alignment. This leads to more symmetrical and consistent higher surface contact areas (a better "cold weld"), with less micro-motion and therefore less fretting and corrosion. In summary some embodiments may include a different geometrical shape for the trunnion (i.e.: hexagonal as opposed to circular) that allows "early guidance" and better seating protecting against early macroscopic mis-alignment. One possible way that this may be accomplished more easily is with 3D printing, however, it may also be accomplished with standard manufacturing techniques. Alternatively, or in addition, to such additive manufacturing, subtractive manufacturing techniques may also be employed.

Another possible advantage of 3D printing is the ability to change the structure, density and porosity of the crystalline metals. Some embodiments may include a control of a crystalline structure of metals imbued to a metal part that is hard and brittle (higher modulus) and part that is springy and soft (lower modulus). This may allow improved capabilities in construction of prosthesis that are more natural and more closely resemble the human anatomy. For example finite element analysis model assessing five trunnion-head junctions, Lavernia et al. J of Arthroplasty 30(6):1085 determined that not only was the area of maximum stress located on a medial aspect of the femoral neck, but also that the maximum stress in this area increased with larger head diameters.

Figure 8:
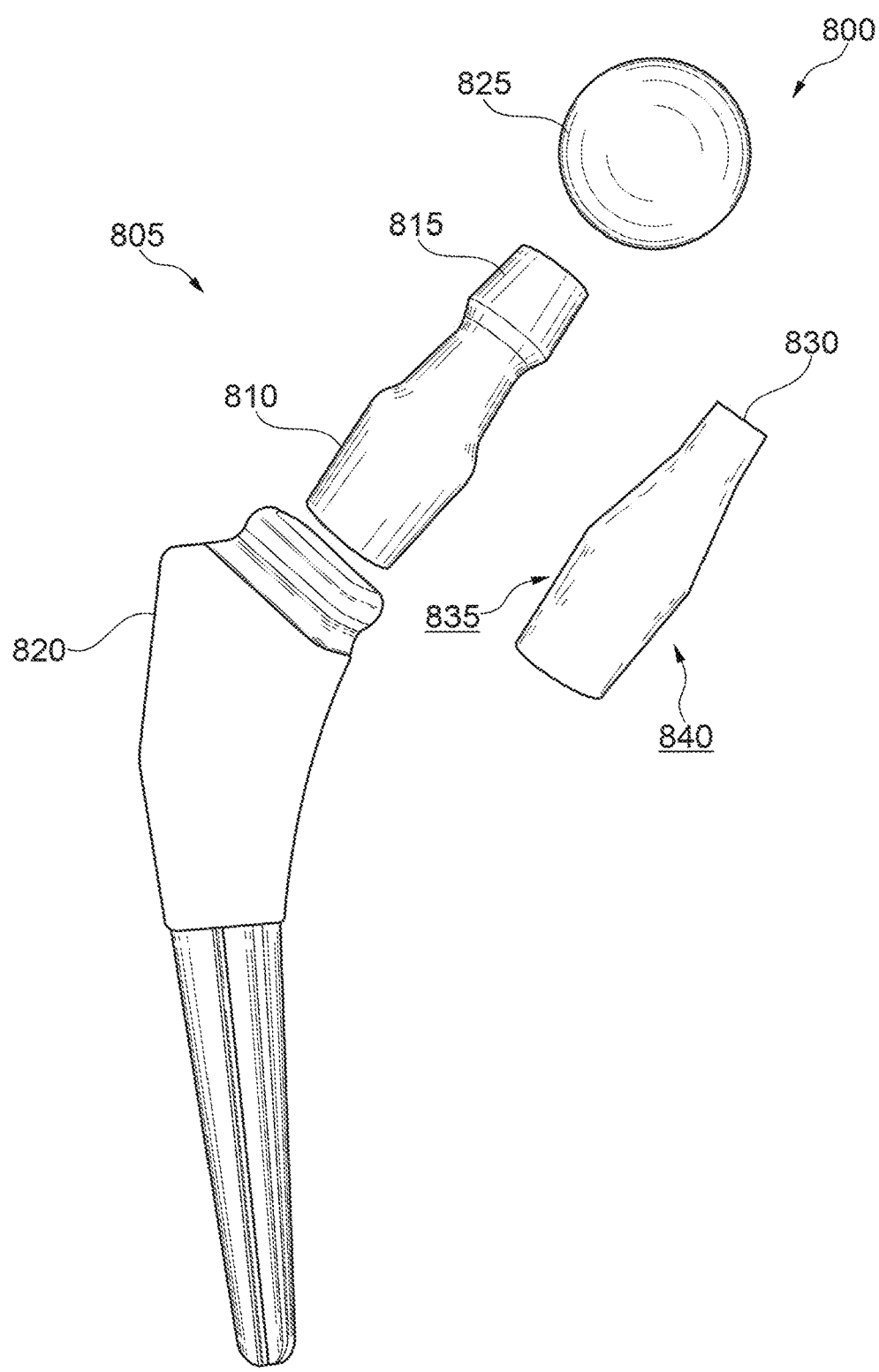
FIG. 8 illustrates a side elevation view of a modular prosthesis assembly having a tailored stiffness profile.

FIG. 8 illustrates a modular prosthesis assembly 800 in an unassembled mode 805. Mode 805 illustrates three components of assembly 800: a neck 810 which includes a trunnion 815, a body 820 (which sometimes may be referred to as a stem in specific assemblies 800), and a head 825.

Also illustrated is a stiffness profile 830 for neck 810. In profile 830, different localized regions may reflect a more or less "stiff" composition, arrangement, structure, or the like as compared to other localized regions. For example, a first lateral edge 835 may be less stiff as compared to a second lateral edge 840 (which is more stiff) opposite of first lateral edge 835. Other embodiments may apply different profiles to additional and/or other portions of a modular assembly such as assembly 800. In some embodiments, the profile(s) is/are designed to replicate the tissue profile into which the assembly is being installed. In other embodiments, the profiles may also, or alternatively, produce a profile that improves upon the natural characteristics of the tissue.

This brings up the possibility of creating a prosthesis that has multidimensional stiffness. U.S. provisional patent application Ser. No. 15/055,942, filed 29 Feb. 2016 and titled "ACETABULAR CUP IMPLANTATION SYSTEMS AND METHODS" and hereby expressly incorporated by reference thereto in its entirety for all purposes has previously described creation of an acetabular cup that has a two-dimensional or stiffness properties, which allow creation of undulatory motion and propagation of impulsive energy. This property may allow the cup to have a preference for insertion. Some embodiments of the present invention may use this technology for production of a trunnion that closely resembles the structure of the human femoral neck, with varied structural properties and modulus of elasticity. The medial calcar in the human femoral neck is designed by nature to resist compressive forces and the lateral femoral neck is more exposed to tensile stresses. A stiffness profile may match this arrangement.

Figure 9:
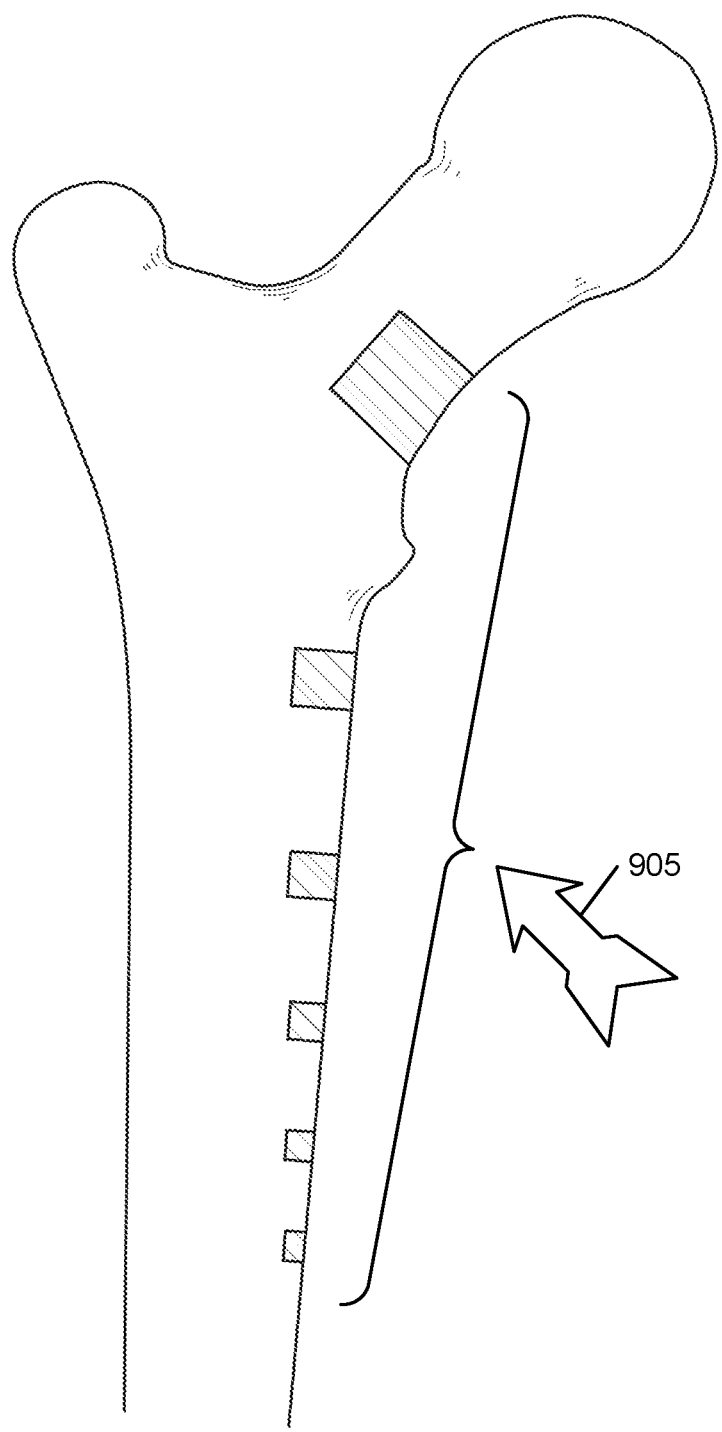
FIG. 9 illustrates a view of a portion of a bone that will receive a modular prosthesis assembly including a natural stiffness profile.
Figure 10:
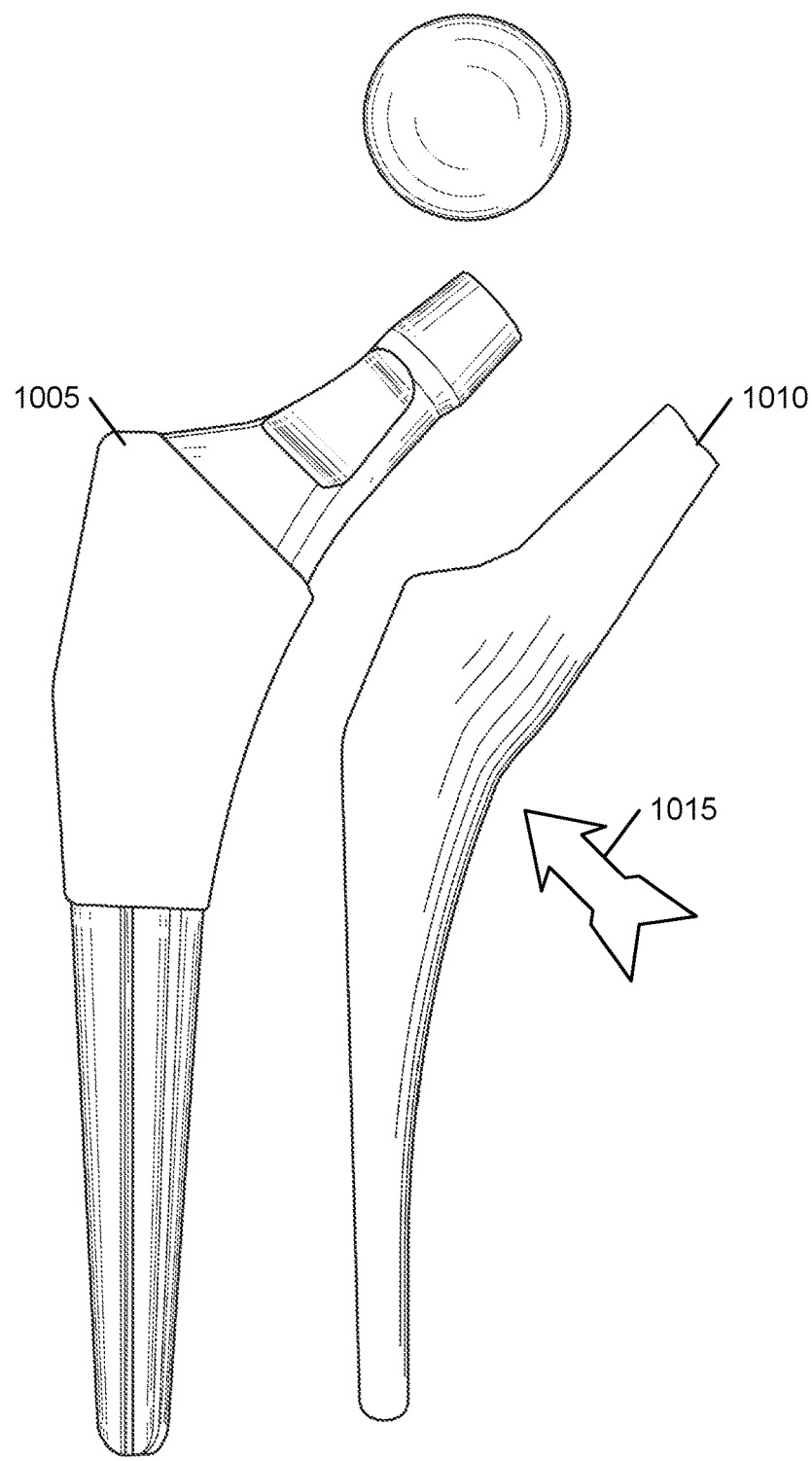
FIG. 10 illustrates a side elevation view of a modular prosthesis assembly having a tailored stiffness profile matching the bone it is to installed into (e.g., the portion of bone of FIG. 9)

FIG. 9 illustrates a view of a portion of a bone that will receive a modular prosthesis assembly including a natural stiffness profile 905. FIG. 10 illustrates a side elevation view of a modular prosthesis assembly 1005 having a tailored stiffness profile 1010 simulating the bone it is to be installed into (e.g., the portion of bone of FIG. 9) by varying material properties 1015 of assembly 1005 in addition to bulk level geometrical parameters of assembly 1005. While the material properties and bulk level geometrical parameters of assembly 1005 cooperate to produce a final aggregated stiffness profile, for a particular geometric design, a possibility of varying material properties at minute localized regions throughout the prosthesis allows for a virtually unlimited number of stiffness permutations and range that may not be obtained by bulk geometric variation alone. There may be many different ways to achieve these varying localized variations in non-bulk geometric material properties, disclosed and described herein is a use of additive manufacturing such as three-dimensional printing.

Studies have shown that "flexural rigidity" is an important factor in inducing corrosion because it affects elastic-based micro-motion or fretting that arises at the modular junction when applied loads or moments cause elastic strain. These strains generate stretching on the tensile side and compression on the compressive side, causing displacement of approximately 5 to 40 microns in line with observation of fretting scars (Gilbert J L, Mali S Medical Implant corrosion: electrochemistry at metallic biomaterial surfaces Degradation of Implant Materials. Springer, 2012, pp. 1-28. Some embodiments of the present invention may be that the femoral trunnion be made in a manner to replicate and/or enhance this structure, using 3D printing technology, with higher density in the calcar/medial region to resist compressive loads and lower density in the lateral neck to respond to tensile stresses. Some embodiments that include a formation of a multi-dimensionally stiff trunnion may diminish the micro-motion and fretting that occurs at the trunnion/head interface.

Figure 11:
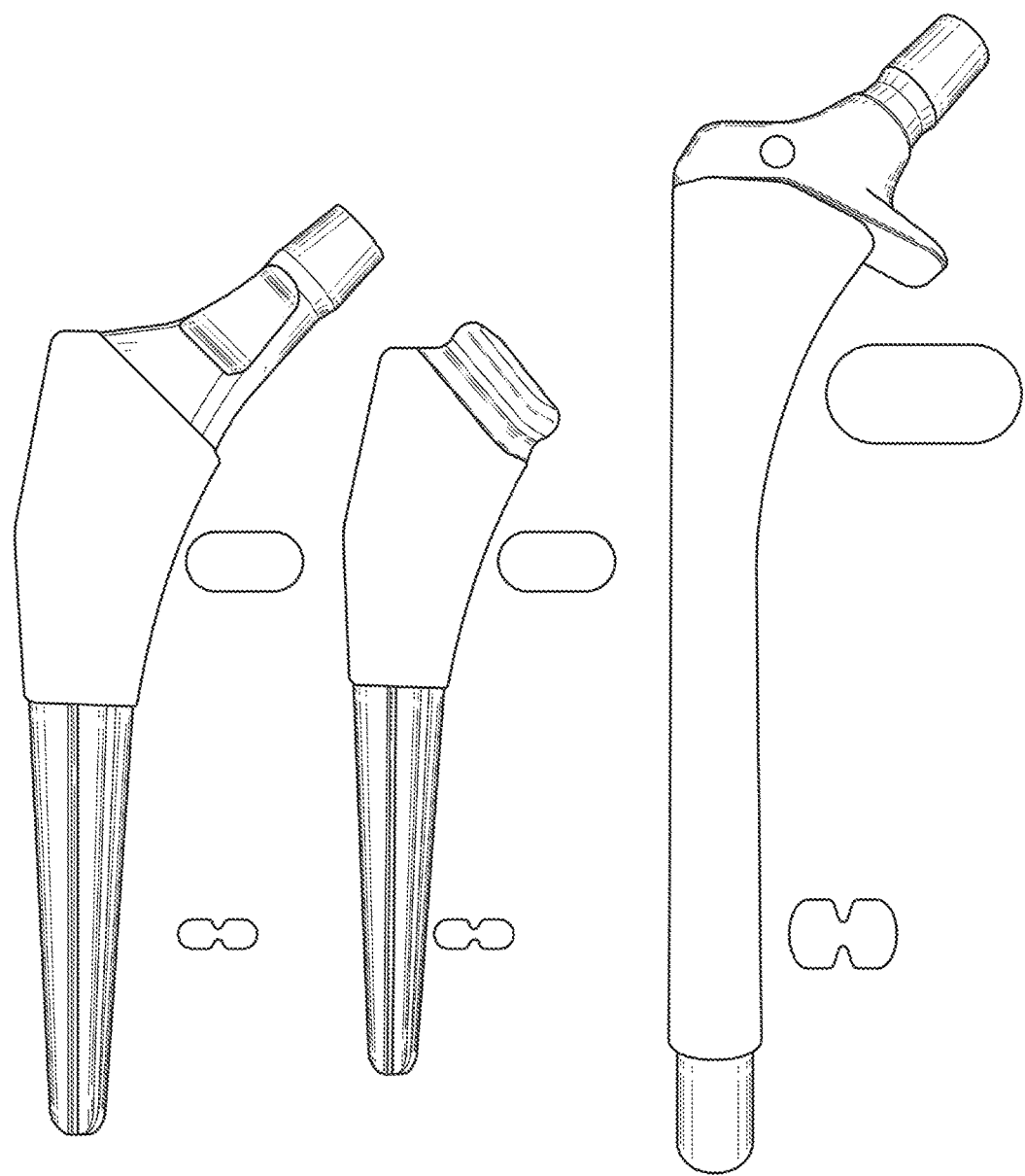
FIG. 11 illustrates a side elevation view of an alternative set of modular prosthesis assemblies having a variable stiffness profile.
Figure 12:
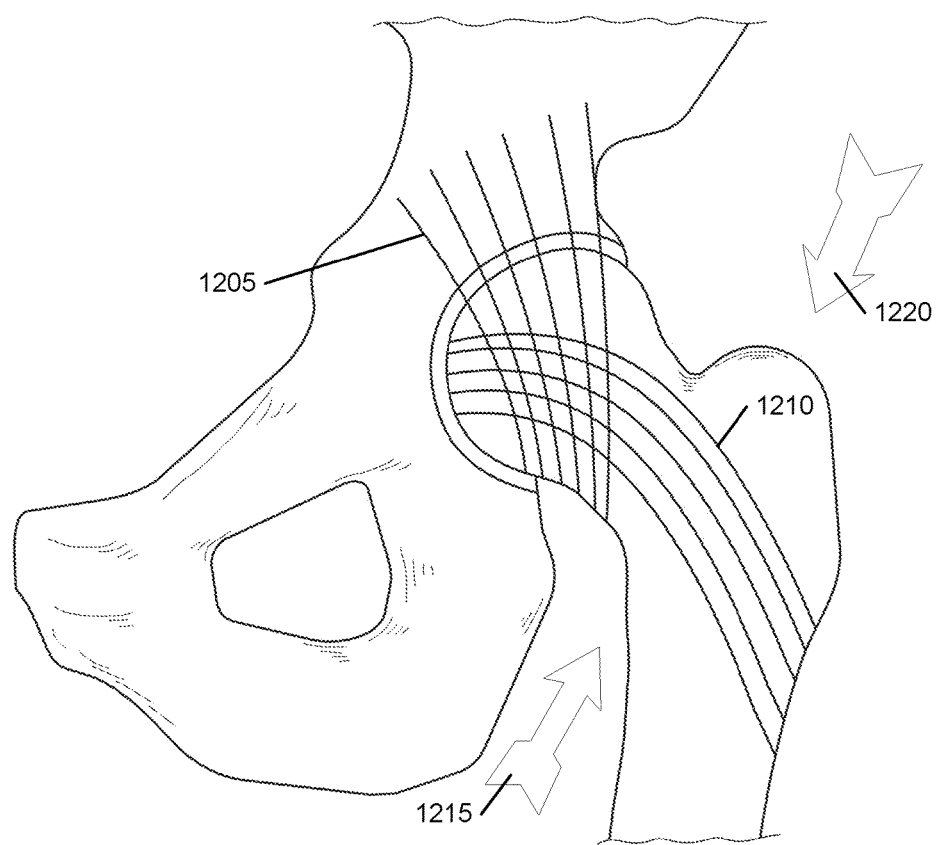
FIG. 12 illustrates a set of compressive and tensile force lines in a representative joint that can be matched by tailored prosthesis assemblies as described herein.

FIG. 11 illustrates a side elevation view of an alternative set of modular prosthesis assemblies, each having a variable stiffness profile set by bulk level geometric properties; and FIG. 12 illustrates a set of compressive 1205 and tensile 1210 force lines in a representative joint that can be simulated by tailored prosthesis assemblies as described herein. For example, a first region 1215 including medial (principal) compressive trabeculae and a second region 1220 including principal tensile trabeculae.

In the same light the stem of the femoral component may be made taking care to vary the stiffness of the whole stem from proximal to distal, simply by changing the porosity and density of the crystalline metal (now allowable through 3D printing). In this way stresses are better transferred from prosthesis to bone leading to less unwanted wear and bone resorb ion due to stress shielding. We note that until now the stiffness properties of the femoral stem (and all implants in general have been altered by changing the geometry and cross sectional area). Some embodiments may include a new method of changing the stiffness of any modular assembly such as a prosthesis). A potentially important implementation is in the creation of multi-dimensional femoral stem. This can apply to femoral and tibial nails commonly used in trauma.

Features of one or more embodiments of the present invention may include one or more of the following:
1) Manufacture and/or use of a Force Imparting machine that delivers standardized amounts of force (magnitude), and at a precise direction (co-axial), some of which may include explicit elements illustrated herein. In addition to the incorporated patent references, U.S. Patent Application No. 62/277,294 filed 11 Jan. 2016, hereby expressly incorporated by reference thereto in its entirety for all purposes, describes some installation and force-imparting devices, some of which may be adapted using some of the principles described and/or illustrated herein. For example, an installation of a head onto a trunnion and/or an installation of a trunnion onto a body/stem.
2) A new design for a trunnion head and trunnion stem interface, with an introduction of angularity (sharp angles) and hence "early guidance system" protecting against macro and (subsequently) micro mis-alignment.
3) Manufacture of a trunnion and trunnion interface through different manufacturing techniques, for example additive rather than subtractive techniques (e.g., 3D printing).
4) Multidimensional stiffness of a trunnion that more closely resembles the mechanical properties of the human femoral neck. Stiffer on the load bearing medial neck and more elastic on tensile lateral side. As discussed further, the stiffness may be varied by components of the material while preserving geometry congruent with natural tissue/bone as some systems may alter a cross-sectional geometry, which departs from the congruence with the natural tissue, to achieve variable stiffness which better matches the replaced tissue.
5) A femoral head can, similar to the acetabular cup described in incorporated patent application, be made with two-dimensional stiffness (e.g., cross-helical arrangement in the eel's skin) or (e.g., longitudinal struts that are more flexible and horizontal bands that are more rigid) in order to allow undulatory motion and which may produce a preference/bias for insertion/assembly.
6) Stiffness of implants in general and femoral components have been so far controlled by changing the geometry and cross-sectional area of the implant particularly at the tip of the prosthesis. Some embodiments may include varying the "stiffness" of the implant by changing the modulus of elasticity of the material (e.g., metal) by controlling the density and porosity of the material (e.g., crystalline metal) vis-à-vis 3D printing. Multi-dimensional prosthesis can address many of our current problems by mimicking our natural engineering. Specifically, certain parts of our proximal femur is very stiff and certain parts is less stiff and more flexible. Simulation/replication of these properties in the prosthetic femoral stem/neck/head junction, may alleviate many of the unwanted wear patterns currently seen in other systems.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An implant for at least a partial insertion into a portion of a bone, the portion of bone having a bone variable material properties profile, comprising:
 a first portion configured for installation into the portion of bone, said first portion including a first reference location, a second reference location spaced apart from said first reference location, and a first portion variable material properties profile including said first reference locations with said first portion variable material properties profile different from and generally compatible with the bone variable material properties profile and with said first portion variable material properties profile between said reference locations including a monotonically changing stiffness when extending from said first reference location to said second reference location;
 a second portion, coupled to said first portion, configured to extend from the portion of bone when said first portion is installed in the portion of bone.

2. The implant of claim 1 wherein said first portion includes an element selected from the group consisting of a prosthesis, a nail, an external fixator, an implant, a plate, and combinations thereof.

3. The implant of claim 1 wherein the bone variable materials property profile includes a varying materials property gradient responsive to changes in a set of material properties over a first region including said reference locations, wherein said first portion is configured for installation proximate said first region, and wherein said first portion variable material properties profile matches said varying material properties gradient.

4. The implant of claim 3 wherein said first region extends from a first lateral edge of the bone to a second lateral edge of the bone, wherein said first lateral edge includes said first reference location, and wherein said second lateral edge includes said second reference location.

5. The implant of claim 3 wherein said first region extends from a first end of the bone to a middle portion of the bone wherein said middle portion of the bone is located about halfway between said first end and a second end of the bone, wherein one of said ends includes said first reference location, and wherein said middle portion includes said second reference location.

6. The implant of claim 3 wherein said first portion includes a first portion material and wherein said varying material properties gradient of said first portion variable material properties profile includes variations in a material grain size of said first portion material.

7. The implant of claim 3 wherein said first portion includes a first portion material and wherein said varying material properties gradient of said first portion variable material properties profile includes variations in a porosity of said first portion material.

8. The implant of claim 3 wherein said first portion includes a first portion material and wherein said varying material properties gradient of said first portion variable material properties profile includes variations in a crystalline structure of said first portion material.

9. The implant of claim 1 including a modular prosthesis having said first portion including a stem portion and said modular prosthesis having said second portion including a discrete head portion configured to be joined to said stem portion.

10. The implant of claim 1 wherein the bone variable material properties profile includes a metric indicating a resistance of the bone to an elastic deformation selected from the group consisting of an elastic modulus, a Young's modulus, a shear modulus, a bulk modulus, a Poisson's ratio, a Lame's first parameter, a P-wave modulus, and combinations thereof.

* * * * *